(12) United States Patent
Romeo et al.

(10) Patent No.: US 6,599,883 B1
(45) Date of Patent: Jul. 29, 2003

(54) NASAL DELIVERY OF XYLITOL

(75) Inventors: Vincent D. Romeo, Massapequa, NY (US); Charanjit R. Behl, Hauppauge, NY (US)

(73) Assignee: Nastech Pharmaceutical Company, Inc., Hauppauge, NY (US)

( * ) Notice: Subject to any disclaimer, the term of this patent is extended or adjusted under 35 U.S.C. 154(b) by 0 days.

(21) Appl. No.: 09/429,255

(22) Filed: Oct. 29, 1999

Related U.S. Application Data
(60) Provisional application No. 60/106,388, filed on Oct. 30, 1998.

(51) Int. Cl.$^7$ ............................................. A61K 31/7004
(52) U.S. Cl. ........................................................ 514/23
(58) Field of Search .............................................. 514/23

(56) References Cited

U.S. PATENT DOCUMENTS

| | | | |
|---|---|---|---|
| 4,374,122 A | 2/1983 | Stroz et al. ................... 424/48 |
| 4,419,346 A | 12/1983 | Stroz et al. .................. 424/151 |
| 4,457,921 A | 7/1984 | Stroz et al. .................. 424/180 |
| 4,508,713 A | 4/1985 | Stroz et al. ................... 514/60 |
| 4,525,363 A | 6/1985 | D'Amelia et al. .............. 426/3 |
| 5,514,673 A | 5/1996 | Heckenmüller et al. ..... 514/177 |
| 5,612,053 A | 3/1997 | Baichwal et al. ............ 424/440 |
| 5,719,196 A | 2/1998 | Uhari et al. ............... 514/738 |
| 5,766,620 A | 6/1998 | Heiber et al. ................ 424/436 |
| 5,780,431 A | 7/1998 | Ho et al. ........................ 514/12 |
| 5,785,976 A | 7/1998 | Westesen et al. ........... 424/400 |

FOREIGN PATENT DOCUMENTS

| | | | |
|---|---|---|---|
| WO | 87/05213 | * | 9/1987 |
| WO | 9729738 | * | 8/1997 |

OTHER PUBLICATIONS

Kontiokari et al., Antimicrobial Agents and Chemotherapy, 39(8), 1820–3 (abstract), Sep. 1995.*

*Pediatrics,* vol. 102, No. 4, Oct. 1998, pp 879–972; "A Novel Use of Xylitol Sugar in Preventing Acute Otitis Media". Matti Uhari, MD; Tero Kontiokari, MD; and Marjo Niemelä. MD.

* cited by examiner

*Primary Examiner*—Phyllis G. Spivack
(74) *Attorney, Agent, or Firm*—Woodcock Washburn LLP

(57) ABSTRACT

The present invention is a method and pharmaceutical composition for prevention and/or treatment of upper respiratory infections including otitis media by nasal administration of xylitol.

26 Claims, 1 Drawing Sheet

NASAL DELIVERY OF XYLITOL

The present invention claims priority to U.S. provisional application No. 60/106,388, filed Oct. 30, 1998.

FIELD OF THE INVENTION

The present invention relates generally to the art of intranasal delivery of bio-effecting agents to a mammal and, in particular, to an intranasal treatment and composition which rely on the effects of sugar alcohols, especially xylitol.

BACKGROUND OF THE INVENTION

Sugar alcohols, also known as polyols, are utilized in a variety of fields. The use of these polyhydric alcohols, such as sorbitol, mannitol, and xylitol, as non-fermentable carbohydrates in place of sucrose and other sugars in chewing gums and confections is known. For the most part sugar alcohols have been known and used based on their unique, substantially non-nutritional sweetening properties.

For example, xylitol, which is a five carbon chain classified as a polyol or sugar alcohol (commonly known as birch sugar because it can be derived from birch), is used as a sweetener because it possesses a sweetness equivalent to that of sucrose. Due to its five-carbon sugar alcohol structure, xylitol is unsuitable as a source of energy for most oral microorganisms. Regular consumption of xylitol has also been shown to reduce the incidence of dental caries. This is primarily attributed to xylitol's ability to inhibit and/or reduce the growth and acid production of *S. mutans*, which is the most important bacterium taking part in the pathomechanism of dental caries.

Xylitol similarly inhibits the growth of *Streptococcus pneumonia* in vitro during its logarithmic growth phase. The *S. pneumonia* bacteria species is believed to be the causative agent of certain types of pneumonia and upper respiratory infections, and is associated with other infectious diseases such as meningitis and sepsis. Furthermore it is believed to account for about 30% of all acute otitis media (AOM) episodes. Nasopharyngeal carriage of pneumococci has been shown to be a predisposing factor for AOM in children in a day care center.

Otitis media involves inflammation of the middle ear portion of the ear. The middle ear, or tympanum, is an irregular cavity which is filled with air, and communicates with the nasopharynx by the eustachian tube. Functionally speaking, the tympanum is traversed by a chain of movable bones, which connect the membrana tympani with the labyrinth, or inner ear, and serve to convey the vibrations communicated to the membrana tympani across the cavity of the tympanum to the internal ear.

Upper respiratory infections including otitis media are very prevalent in children. As mentioned above, many cases are believed to be caused by the *S. Pneumonia* bacteria. U.S. Pat. No. 5,719,196, issued to Uhari et al., has established that by using oral dosages of an effective amount of xylitol, respiratory infections such as otitis media may be effectively treated. The patent discloses that xylitol exhibits a growth inhibiting effect against pneumococci which reduces the pneumococcal carriage rates and also reduces the incidence of infection. The Uhari patent claims oral administration in the form of a solid, liquid, or as a chewing gum.

The nose is a reservoir for infectious agents. It is a source of entry for viral and microbial dissemination to the upper and lower respiratory tracts. The nasal carriage rate in infants can be as high as 70–90%, and declines with age. At three years of age, up to 40% of children carry pneumococci in their nasopharynx. This may explain the higher rate of acute otitis media and respiratory infections in younger children. The major respiratory pathogens, *S. pneumonia, H. influenza* and *S. pyogenes* are commonly found in the nasopharynx of children (45–90%, 15–70% and 3–50%, respectively) and also to a lesser extent in adults (15–25%, 6–40% and 6%, respectively).

It is, therefore, an intention of the present invention to provide improved composition(s) and method for treating respiratory infections including otitis media in mammals (e.g., humans) by nasally administering xylitol.

SUMMARY OF THE INVENTION

The present invention is a method and a composition for preventing and/or treating respiratory infections and otitis media in a mammal, especially human, by nasal administration of xylitol. In order to effectively administer xylitol nasally, it is formulated with one or more pharmaceutically acceptable carriers suitable for intranasal delivery.

Preferably the carrier includes a buffer (to maintain the pH of the composition), a thickening agent, a bioadhesive and a humectant. A pharmaceutically acceptable surfactant and a preservative may also be included along with one or more excipients suitable for a pharmaceutical composition.

Preferable buffers for maintaining the pH of the composition may be selected from the group consisting of acetate, citrate and phosphate buffers.

Preferably, thickening agents may be included and selected from the group consisting of methylcellulose, xantham gum, carboxy methylcellulose, polyvinyl alcohol, hydroxypropyl cellulose, carbomer, starches, chitosans, acrylates, and mixtures thereof. These excipients may also function as bioadhesives.

A suitable humectant can be selected from the group consisting of sorbitol, propylene glycol, glycerol, and mixtures thereof. Additionally, the surfactant can be anionic, cationic, or nonionic and is preferably selected from the group consisting of polyoxyethylene derivatives and fatty acid, partial esters of sorbitol anhydrides. For example, the surfactant can be selected from the group consisting of sodium lauryl sulfate, Tween 80, polyoxyl Stearate, polyoxy ethylene 50, fusieates, bila salts, and Octoxynol.

Preferably, the dosage rate administered to the host can be in an amount of from about 1 mg to about 10 g, more preferably from about 1 mg to about 2 g, and most preferably from about 1 mg to about 1 g. Such dosages can be administered in nasal compositions having a concentration of xylitol of from about 0.001% to about 10% by weight, more preferably from about 0.001% to about 2% by weight, and most preferably from about 0.001% to about 1% by weight.

The regimen of choice includes application of a nasal spray or gel at a frequency rate from once daily to about 4 times per day.

As a result of the present invention, a highly effective and efficient method of treatment for respiratory infections and otitis media is provided by nasal administration of xylitol. The present invention permits the delivery of xylitol more proximal to the biological area requiring treatment than by oral administration.

For a better understanding of the present invention, together with other and further objects and advantages, reference is made to the following detailed description, taken in conjunction with the accompanying examples, and the scope of the invention will be pointed in the appended claims. The following detailed description is not intended to restrict the scope of the invention by the advantages set forth above or by the detailed description.

DETAILED DESCRIPTION OF THE INVENTION

Figure 1:
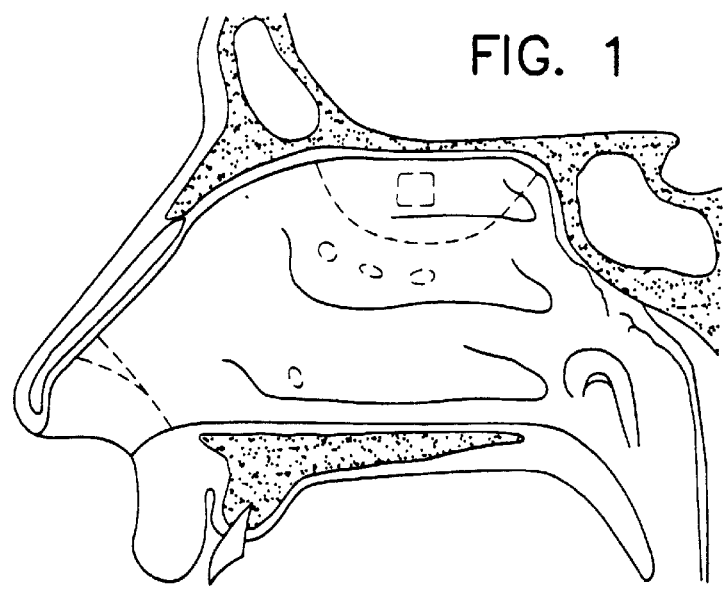
FIG. 1 is a diagram depicting the lateral wall of the nasal cavity of a human.
Figure 2:
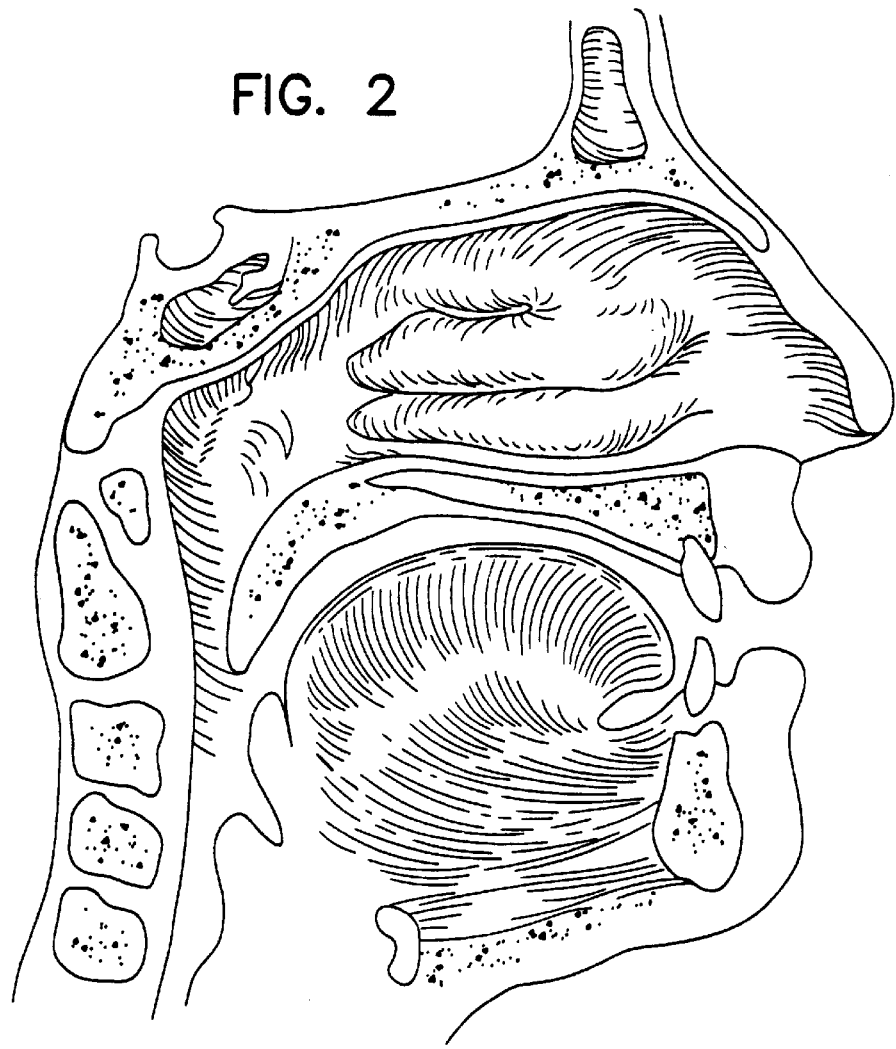
FIG. 2 is a diagram depicting oral administration versus nasal administration for localized delivery.

As demonstrated through FIGS. 1 and 2, anatomically, the nasopharynx is the point at which the nasal passages merge into one. It is also where the floor of the nose bends downward with the superior-posterior surface of the palate. Within the nasopharynx are located the openings of the auditory tubes (eustachian tubes) and the posterior nasal apertures (choane). The oropharynx is located inferior to the nasopharynx and is behind the mouth. By virtue of the anatomic locations of the eustachian tube openings in the nasopharynx, nasal administration of a solution, suspension, gel or powder will result in a more effective exposure of the eustachian tube openings versus administration via the oral route.

While the treatment of otitis media via oral administration of xylitol is known, a more desirable method of treatment is herein provided by nasal administration of xylitol. The eustachian tube, the auditory tube extending from the middle ear to the naso-pharynx, is 3 to 4 centimeters long and lined with mucous membrane. It also is the channel through which the tympanum communicates with the naso-pharynx, and is formed partly of bone, partly of cartilage, and partly of fibrous tissue. Infection of the eustachian tube can lead to the development of otitis media.

The oral pharynx is the part of the alimentary canal which is positioned behind the nose, mouth, and larynx. It is a musculo-membranous tube, somewhat conical in form, with the base upward and the apex downward, extending from the under surface of the skull to the level of the circoid cartilage in front and that of the invertebral disk between the fifth and sixth cervical vertebrae behind.

Nasal administration of a medicament for treating respiratory infections and otitis media is therefore advantageous because it provides for direct delivery through the nose to the nasopharynx area. Because the nasopharynx area is a cavity communicating directly with the nasal passage and connected to the tympanum by the eustachian tube, topical application provides a more proximal delivery of a medicament for the treatment of infections such as otitis media, which often may start as an infection at the opening of the eustachian tube in the nasopharyngeal area.

The present invention contemplates at least two primary modes of treatment of otitis media via nasal administration: namely (i) bathing, and (ii) adhesion delivery methods. The bathing method encompasses the use of the active agent of the medicament contained within a dilute pharmaceutically acceptable carrier suitable for nasal administration. The term dilute used herein refers to a less viscous, more fluid medicament composition. The medicament can be a predominantly aqueous composition comprising water, the active agent xylitol, and other pharmaceutically-acceptable carrier components.

Treatment with such a bathing medicament contemplates direct delivery to the nasopharynx, and subsequent bathing in the nasal-pharyngal area. As a result of using a free-flowing low viscosity fluid medicament, a rapid and concentrated application of the medicament ensues; a significant improvement over the random application of active ingredient provided by oral administration via chewing gum, tablet, syrup, or the like. A preferred formulation for use in the bathing method includes a solution spray composition.

The adhesion method of application of a medicament encompasses the use of a more viscous medicament, such as a gel. The medicament may be provided with or without a bio-adhesive agent. This method of treatment relies on the adhesion of the medicament to the nasal mucous membrane and a slow migration to the naso-pharyngal area. This provides a more gradual and steady application of the active agent of the medicament, rather than the flooding provided in the bathing method by a formulation without bioadhesive properties. A preferred formulation for use in the adhesion method includes gel type matrices and thick, viscous solutions.

It is believed that both methods of nasal administration of a medicament for preventing and/or treating infection provide a more effective method than oral administration of such a medicament. Oral administration provides a more random occurance of application to the problem area, in that some effective dosage of the active treating agent may migrate from the mouth to the eustachian tube area. Both methods of nasal administration provide a more direct and, therefore, more effective method of treatment. Higher concentrations of the medicament reach the target treatment area, at a more rapid rate via nasal administration.

Moreover, nasal administration of xylitol provides for a more efficient localized delivery without unwanted side effects associated with introduction of sugar alcohols to the gastro-intestinal system.

EXAMPLES

The following are examples of compositions which may be prepared for nasal administration of a xylitol medicament composition. Xylitol is the preferred active agent of the medicament, but the use of other sugar alcohols is also contemplated within the scope of the present invention.

Example 1

A composition is prepared for a dilute bathing formulation of xylitol for nasal delivery. The concentration of xylitol in the solution may be 10%–60% by weight/volume. This corresponds to 10–60 grams of xylitol per 100 ml of solution. xylitol is soluble in solution up to 64.2 grams per 100 ml of solution.

The following components were used to prepare the nasal delivery composition of Example 1:

TABLE 1

| COMPONENTS | AMOUNT (g/100 ml) |
| --- | --- |
| Xylitol | 10–60 |
| Sodium Citrate Dihydrate, U.S.P. | 0.50 |
| Citric Acid Anhydrous, U.S.P | 0.20 |
| Benzalkonium Chloride (50%), N.F. | 0.04 |
| HCl or NaOH | Variable to adjust pH to 3.0, 5.0, and 7.0 |
| Purified Water, U.S.P. q.s. | 100 ml |

The dosage range used for the formulation is anywhere from 0.1–0.4 ml per dose. It is preferred to administer dosages 1–4 times daily. Depending on the amounts of xylitol added to the solution a 0.1 ml dose would therefore deliver anywhere from 10–60 mgs of xylitol. Accordingly, a 0.4 ml dose of the nasal spray would administer anywhere from 4–240 mgs of xylitol.

A composition of Example 1 consists of xylitol, which is the active ingredient in the medicament, a buffer system, (consisting of sodium citrate dihydrate, citric acid anhydrous, and hydrochloric acid or sodium hydroxide), as well as an antimicrobial preservative, benzalkonium chloride (50%), all dissolved in 100 mls of water. The composition of Example 1 is considered a bathing mist, as it has no thickening agents added to the solution to provide more viscosity to the composition. Additionally, the formulation of Example 1 is used to form three different medicament compositions. The compositions vary depending on the pH, as noted in the amount of HCl or NaOH added. Three different formulations are contemplated for example 1; one with a pH of 3.0, one with a pH of 5.0, and one with a pH of 7.0.

The following are additional examples of xylitol medicament compositions which may be formed according to the present invention. In all of the following examples, the concentration of xylitol is consistent, as are the buffer components, and the antimicrobial preservative component (benzoalkonium chloride (50%)) concentration. Accordingly, the preferred dosage and amount of xylitol administered nasally from the composition is consistent throughout the following examples. Additionally, all of the compositions in the following examples may be prepared at a pH of 3.0, 5.0, or 7.0.

Example 2

TABLE 2

| COMPONENTS | AMOUNT (g/100 ml) |
| --- | --- |
| Xylitol | 10–60 |
| Sodium Citrate Dihydrate, U.S.P. | 0.50 |
| Citric Acid Anhydrous, U.S.P. | 0.20 |
| Glycerin (96%) U.S.P. | 2.0 |
| Benzalkonium Chloride (50%), NF | 0.04 |
| HCl or NaOH | Variable to adjust pH to 3.0, 5.0, and 7.0 |
| Purified Water, U.S.P. q.s. | 100 ml |

The composition of example 2 contains the additional component of glycerin. Glycerin serves as a humectant in the composition.

Example 3

TABLE 3

| COMPONENTS | AMOUNT (g/100 ml) |
| --- | --- |
| Xylitol | 10–60 |
| Sodium Citrate Dihydrate, U.S.P. | 0.50 |
| Citric Acid Anhydrous, U.S.P. | 0.20 |
| Hydroxy Propyl Cellulose, N.F. | 2.0 |
| Benzalkonium Chloride (50%), NF | 0.04 |
| HCl or NaOH | Variable to adjust pH to 3.0, 5.0, and 7.0 |
| Purified Water, U.S.P. q.s. | 100 ml |

The composition of Example 3 additionally includes hydroxy propyl cellulose. Hydroxy propyl cellulose serves as a humectant, as well as a thickening agent to provide a more viscous composition. The compositions of Example 3 are consequently more viscous than the compositions of Examples 1 and 2. The compositions of Example 3 are gels which would provide greater adhesion in the intranasal area and within the delivery method of the present invention.

Example 4

TABLE 4

| COMPONENTS | AMOUNT (g/100 ml) |
| --- | --- |
| Xylitol | 10–60 |
| Sodium Citrate Dihydrate, U.S.P. | 0.50 |
| Citric Acid Anhydrous, U.S.P. | 0.20 |
| Glycerin 96%, U.S.P. | 10 |
| Hydroxy Propyl Cellulose, N.F. | 2.0 |
| Benzalkonium Chloride (50%), NF | 0.04 |
| HCl or NaOH | Variable to adjust pH to 3.0, 5.0, and 7.0 |
| Purified Water, U.S.P. q.s. | 100 ml |

Example 5

TABLE 5

| COMPONENTS | AMOUNT (g/100 ml) |
| --- | --- |
| Xylitol | 10–60 |
| Sodium Citrate Dihydrate, U.S.P. | 0.50 |
| Citric Acid Anhydrous, U.S.P. | 0.20 |
| Methylcellulose, U.S.P. | 2.0 |
| Benzalkonium Chloride (50%), NF | 0.04 |
| HCl or NaOH | Variable to adjust pH to 3.0, 5.0, and 7.0 |
| Purified Water, U.S.P. q.s. | 100 ml |

Similar to the compositions of Example 3, methylcellulose acts as a surfactant, as well as thickening agent in the compositions of Example 5. The compositions of Example 5 are also similarly gels with adhesive properties.

Example 6

TABLE 6

| COMPONENTS | AMOUNT (g/100 ml) |
| --- | --- |
| Xylitol | 10–60 |
| Sodium Citrate Dihydrate, U.S.P. | 0.50 |
| Citric Acid Anhydrous, U.S.P. | 0.20 |
| Glycerin 96%, U.S.P. | 10 |
| Methylcellulose, U.S.P. | 2.0 |
| Benzalkonium Chloride (50%), NF | 0.04 |
| HCl or NaOH | Variable to adjust pH to 3.0, 5.0, and 7.0 |
| Purified Water, U.S.P. q.s. | 100 ml |

While there have been described what are presently believed to be the preferred embodiments of the invention, those skilled in the art will realize that changes and modifications may be made thereto without departing from the spirit of the invention, and it is intended to include all such changes and modifications as fall within the true scope of the invention.

What is claimed is:

1. A pharmaceutical composition for preventing and/or treating upper respiratory infections in a mammal comprising an active agent consisting essentially of xylitol in combination with a pharmaceutically acceptable carrier suitable for intranasal delivery.

2. A pharmaceutical composition according to claim 1 wherein said carrier includes a component selected from the group consisting of a buffer to maintain the pH of said composition, a pharmaceutically acceptable thickening agent, a humectant, and a pharmaceutically acceptable surfactant, and combinations thereof.

3. A pharmaceutical composition according to claim 2 further comprising one or more pharmaceutical excipients.

4. A pharmaceutical composition according to claim 3 further comprising a pharmaceutically acceptable preservative.

5. A pharmaceutical composition according to claim 2, wherein said buffer is selected from the group consisting of acetate, citrate, and phosphate buffers.

6. A pharmaceutical composition according to claim 2 wherein said thickening agent is selected from the group consisting of methyl cellulose, xanthan gum, carboxymethyl cellulose, hydroxypropyl cellulose, carbomer, and mixtures thereof.

7. A pharmaceutical composition according to claim 2 wherein said humectant is selected from the group consisting of sorbitol, propylene glycol, glycerol, and mixtures thereof.

8. A pharmaceutical composition according to claim 2 wherein said surfactant is selected from the group consisting of polyoxyethylene derivatives and fatty acid partial esters of sorbitol anhydrides.

9. A pharmaceutical composition according to claim 2 wherein said surfactant is selected from the group consisting of sodium lauryl sulfate, Tween 80, Polyoxyl 40 Stearate, Polyoxy ethylene 50 Stearate, fusieates, bile salts, and Octoxynol.

10. A pharmaceutical composition according to claim 2 wherein said surfactant is selected from the group consisting of anionic, cationic, and nonionic surfactants.

11. A pharmaceutical composition according to claim 2 further comprising a bioadhesive.

12. A pharmaceutical composition according to claim 11 wherein said bioadhesive is selected from the group consisting of starches, polyvinyl alcohol, chitosans, gums, and acrylates.

13. A method of preventing and/or treating upper respiratory infections, in a mammal in need thereof comprising nasally delivering to the mammal an active agent consisting essentially of xylitol in a pharmaceutically acceptable carrier suitable for nasal delivery.

14. A method according to claim 13 wherein said carrier comprises a buffer to maintain the pH of said composition, a pharmaceutically acceptable thickening agent, a humectant, and a pharmaceutically acceptable surfactant.

15. A method according to claim 14 further comprising one or more pharmaceutical excipients.

16. A method according to claim 15 further comprising a pharmaceutically acceptable preservative.

17. A method according to claim 14 wherein said buffer is selected from the group consisting of acetate, citrate, and phosphate buffers.

18. A method according to claim 14 wherein said thickening agent is selected from the group consisting of methyl cellulose, xantham gum, carboxymethyl cellulose, hydroxypropyl cellulose, carbomer, and mixtures thereof.

19. A method according to claim 14 wherein said humectant is selected from the group consisting of sorbitol, propylene glycol, glycerol, and mixtures thereof.

20. A method according to claim 14 wherein said surfactant is selected from the group consisting of polyoxyethylene derivatives and fatty acid partial esters of sorbitol anhydrides.

21. A method according to claim 14 wherein said surfactant is selected from the group consisting of sodium lauryl sulfate, Tween 80, Polyoxyl 40 Stearate, Polyoxy ethylene 50 Stearate, fusieates, bile salts, and Octoxynol.

22. A method according to claim 14 wherein said surfactant is selected from the group of anionic, cationic, and nonionic surfactants.

23. The method of claim 13 wherein the dosage rate of the medicament administered to a host is in the amount of from 1 mg to about 10 g.

24. The method of claim 13 wherein the medicament contains concentrations of xylitol in the range of from about 0.001% to about 10% by weight.

25. The method of claim 13 wherein the administration rate comprises administrating said medicament at a rate of about once daily to about 4 times per day.

26. A method according to claim 13 wherein said upper respiratory infection is otitis media.

* * * * *